(12) United States Patent
Fisher

(10) Patent No.: US 11,389,398 B2
(45) Date of Patent: Jul. 19, 2022

(54) GASTRORETENTIVE TREATMENT OF NOCTURNAL SYMPTOMS AND MORNING AKINESIA IN SUBJECTS WITH PARKINSON'S DISEASE

(71) Applicant: Clexio Biosciences Ltd., Jerusalem (IL)

(72) Inventor: Richard Fisher, Jerusalem (IL)

(73) Assignee: Clexio Biosciences Ltd., Jerusalem (IL)

( * ) Notice: Subject to any disclaimer, the term of this patent is extended or adjusted under 35 U.S.C. 154(b) by 105 days.

(21) Appl. No.: 16/874,274

(22) Filed: May 14, 2020

(65) Prior Publication Data

US 2020/0360273 A1     Nov. 19, 2020

Related U.S. Application Data

(60) Provisional application No. 62/858,018, filed on Jun. 6, 2019, provisional application No. 62/847,542, filed on May 14, 2019.

(51) Int. Cl.
| | | |
|---|---|---|
| *A61K 9/00* | (2006.01) | |
| *A61P 25/16* | (2006.01) | |
| *A61K 9/20* | (2006.01) | |
| *A61K 31/198* | (2006.01) | |
| *A61K 38/51* | (2006.01) | |

(52) U.S. Cl.
CPC .......... *A61K 9/0065* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 31/198* (2013.01); *A61K 38/51* (2013.01); *A61P 25/16* (2018.01)

(58) Field of Classification Search
CPC ...... A61K 9/00; A61K 31/198; A61K 9/0065; A61K 38/1558; A61P 25/16; A61P 25/00
See application file for complete search history.

(56) References Cited

U.S. PATENT DOCUMENTS

| | | | |
|---|---|---|---|
| 4,126,672 A | 11/1978 | Sheth et al. | |
| 4,735,804 A | 4/1988 | Caldwell et al. | |
| 4,814,179 A | 3/1989 | Bolton et al. | |
| 5,002,772 A | 3/1991 | Curatolo et al. | |
| 9,072,663 B2 * | 7/2015 | Navon ................. | A61K 9/2886 |
| 10,987,313 B2 * | 4/2021 | Hsu ...................... | A61K 9/4808 |

(Continued)

FOREIGN PATENT DOCUMENTS

| | | |
|---|---|---|
| EP | 1238663 A2 | 9/2002 |
| EP | 1915990 A1 | 4/2008 |

(Continued)

OTHER PUBLICATIONS

Stuebner, et al., "Twenty-four Hour Non-Invasive Ambulatory Blood Pressure and Heart Rate Monitoring in Parkinson's Disease", Frontiers in Neurology, May 15, 2013, 14 pages.

(Continued)

*Primary Examiner* — Carlos A Azpuru
(74) *Attorney, Agent, or Firm* — BakerHostetler

(57) ABSTRACT

Provided are methods and compositions for treating nocturnal symptoms of Parkinson's disease, morning akinesia, or associated symptoms thereof in a human subject in need thereof, wherein circulating plasma levels of levodopa are provided for an extended period of time following a period of delay after administration.

10 Claims, 1 Drawing Sheet

(56) References Cited

U.S. PATENT DOCUMENTS

| | | |
|---|---|---|
| 2003/0049325 A1 | 3/2003 | Suwelack et al. |
| 2005/0013863 A1 | 1/2005 | Lim et al. |
| 2011/0066175 A1 | 3/2011 | Gross |
| 2012/0077878 A1 | 3/2012 | Berner et al. |
| 2013/0017264 A1 | 1/2013 | Khandare et al. |

FOREIGN PATENT DOCUMENTS

| | | |
|---|---|---|
| EP | 3398615 A1 | 11/2018 |
| WO | 98/52547 A1 | 11/1998 |
| WO | 99/07342 A1 | 2/1999 |
| WO | 00/38650 A1 | 7/2000 |
| WO | 00/38655 A1 | 7/2000 |
| WO | 01/10419 A1 | 2/2001 |
| WO | 01/58424 A1 | 8/2001 |
| WO | 01/97783 A1 | 12/2001 |
| WO | 02/00213 A1 * | 1/2002 |
| WO | 2003/011255 A1 | 2/2003 |
| WO | 2003/035029 A1 | 5/2003 |
| WO | 2003/037299 A1 | 5/2003 |
| WO | 2003/089506 A1 | 10/2003 |
| WO | 2003/105812 A1 | 12/2003 |
| WO | 2004/032906 A1 | 4/2004 |
| WO | 2005/007074 A2 | 1/2005 |
| WO | 2005/056708 A2 | 6/2005 |
| WO | 2005/079752 A2 | 9/2005 |
| WO | 2005/101983 A2 | 11/2005 |
| WO | 2006/063858 A1 | 6/2006 |
| WO | 2007/072495 A2 | 6/2007 |
| WO | 2007/106960 A1 | 9/2007 |
| WO | 2007/138086 A1 | 12/2007 |
| WO | 2008/027945 A1 | 3/2008 |
| WO | 2008/030830 A2 | 3/2008 |
| WO | 2008/087882 A1 | 7/2008 |
| WO | 2009/144558 A1 | 12/2009 |
| WO | 2009/153632 A1 | 12/2009 |
| WO | 2010/019915 A1 | 2/2010 |
| WO | 2010/035273 A2 | 4/2010 |
| WO | 2011/004799 A1 | 1/2011 |
| WO | 2011/090725 A2 | 7/2011 |
| WO | 2012/004231 A1 | 1/2012 |
| WO | 2012/059815 A1 | 5/2012 |
| WO | 2012/070028 A1 | 5/2012 |
| WO | 2012/159077 A2 | 11/2012 |
| WO | 2013/054285 A1 | 4/2013 |
| WO | 2013/090893 A1 | 6/2013 |
| WO | 2014/014348 A1 | 1/2014 |
| WO | 2014/060952 A1 | 4/2014 |
| WO | 2015/083171 A1 | 6/2015 |
| WO | 2015/187746 A1 | 12/2015 |
| WO | 2016/066256 A1 | 5/2016 |
| WO | 2016/087952 A1 | 6/2016 |
| WO | 2017/096054 A1 | 6/2017 |
| WO | 2018/011181 A1 | 1/2018 |
| WO | 2018/102799 A1 | 6/2018 |
| WO | 2018/232413 A1 | 12/2018 |

OTHER PUBLICATIONS

Suzuki, et al., "Nocturnal Disturbances in Patients with Parkinson's Disease", Nocturnal Disturbances in Patients with Parkinson's Disease Chapter 3, Symptoms of Parkinson's Disease, IntechOpen, 2011, pp. 51-68.

Suzuki, et al., "Sleep Disturbances Associated with Parkinson's Disease", Parkinson's Disease Art ID 219056, 2011, 11 pages.

Wailke, et al., "effect of Controlled-Release Levodopa on the Microstructure of Sleep in Parkinson's Disease", European Journal of Neurology 2011, 18, pp. 590-596.

Wullner, et al., "Requirements for Parkinson's Disease Pharmacotherapy from the Patients' Perspective: A Questionnaire-Based Survey", Curr Med Res Opin. Jul. 2012, pp. 1239-1246.

Yeh, et al., "Pharmacokinetics and Bioavailability of Sinemet CR: A Summary of Human Studies", Neurology 39 (Supple 2), 1989, pp. 25-39.

Zibetti, et al., "Continuous Intraduodenal L-dopa/carbidopa Gel Infusion Improves Nocturnal Sleep in Advanced Parkinson't Disease", Mov. Disord 27, Suppl. 1 ABS 689, 2012, p. S223.

Klausner EA et al: "Novel levodopa gastroretentive dosage form: in-vivo evaluation in dogs", Journal of Controlled Release, Elsevier, vol. 88, No. 1, Feb. 14, 2003 (Feb. 14, 2003), pp. 117-126, XP004409403.

"24-Hour Infusion of Levodopa/Carbidopa Intestinal Gel for Nocturnal Akinesia in Advanced Parkinson's Disease" Movement Disorders 31(4), 2016, pp. 597-598.

"Duopa FDA Approved Labelling" Sep. 15, 2016, 107 pages.

"Rytary FDA Approved Labelling" Oct. 27, 2016, 18 pages.

"Simemet CR FDA Approved Labelling", Jul. 17, 2014, 12 pages.

Alatriste-Booth, et al., "Prevalence and Correlates of Sleep Disorders in Parkinson's Disease: a Polysomnographic Study", Arq Neuropsiquiatr 2015, 73(3), pp. 241-245.

Amato, et al., "Levodopa-Induced Dyskinesia in Parkinson Disease: Sleep Matters", Annals of Neurology vol. 84, Dec. 2018, pp. 905-917.

Antczak, et al., "Negative Influence of L-dopa on Subjectively Assessed Sleep But Not on Nocturnal Polysomnography in Parkinson's Disease", Pharmacol Rep 2013, 65 (3), Copyright 2013, pp. 614-623.

Baruzzi, et al., "Influence of Meal Ingestion Time on Pharmacokinetics of Orally Administered Levodopa in Parkinsonian Patients", Clinical Neuropharmacology 10(6) 1987, pp. 527-537.

Batla, et al., "Nocturia in Parkinson's Disease: Why Does it Occur and How to Manage", Mov Disord (Clin Prac) 3(5), 2016, pp. 443 451.

Bliwise, et al., "Periodic Leg Movements in Sleep in Elderly Patients with Parkinsonism and Alzheimer's Disease", Eur J Neurol. Jun. 19, 2012, (6), pp. 918-923.

Breen et al., "Sleep and Circadian Rhythm Regulation in Early Parkinson Disease", JAMA Neurol. 71(5), May 2014, pp. 589-595.

Buerger, et al., "Phosphorylated Tau Predicts Rate of Cognitive Decline in MCI Subjects: A comparative CSF Study", Neurology 65 Nov. 2005, pp. 1506-1507.

Chahine, et al., "Association between dopaminergic medications and nocturnal sleep in early-stage Parkinson's disease", Parkinsonism and Related Disorders 19 (2013), pp. 859-863.

Collado-Seidel, et al., "A Controlled Study of Additional sr-L-dopa in L-dopa-Responsive Restless Legs Syndrome With Late-Night Symptoms", Neurology vol. 52(2) Jan. 15, 1999, pp. 285-290.

Contin, et al., "Effect of Meal Timing on the Kinetic-Dynamic Profile of Levodopa/Carbidopa Controlled is Release in Parkinsonian Patients", Eur J Clin Pharmacol (1998) 54, pp. 303-308.

Cruse, et al., "24-hour Levodopa-Carbidopa Intestinal Gel May Reduce Troublesome Dyskinesia in Advanced Parkinson's Disease", NPJ Parkinsons Dis. (2018)4 34, 2018, 5 pages.

Deleu, et al., "Long-Term 24-Hour Duodenal Infusion of Levodopa: Outcome and Dose Requirements", Neurology 66 May 2006, pp. 1611-1612.

Devereux, et al., "The Influence of Density on the Gastrointestinal Transit of Pellets", J. Pharm. Pharmacol. 1990, 42: 501-501, Apr. 24, 1989, pp. 500-501.

Dorozynski, et al., "Gastroretentive Drug Delivery Systems with L-Dopa Based on Carrageenans and Hydroxypropylmethylcellulose", International Journal of Pharmaceutics, vol. 404, Feb. 2011, pp. 169-175.

El-Zahaby, et al., "Formulation and In Vitro Evaluation of Size Expanding Gastro-Retentive Systems of Levofloxacin Hemihydrate", International Journal of Pharmaceutics vol. 464, Apr. 2014, pp. 10-18.

Fertl, et al., "Circadian Secretion Pattern of Melatonin in De Novo Parkinsonian Patients: Evidence for Phase-Shifting Properties of L-Dopa", J Neural Transm [P-D Sect] (1993) 5, pp. 227-234.

French, et al., "A Review of Sleep and Its Disorders in Patients with Parkinson's Disease in Relation to Various Brain Structures", Frontiers in Aging Neuroscience vol. 8 May 2016, Art 114, 17 pages.

(56) References Cited

OTHER PUBLICATIONS

Fujimori, et al., "Preparation of a magnetically-responsive tablet and confirmation of its gastric residence in beagle dogs", S.T.P. Pharma Sciences 4, 6, 1994, pp. 425-430.

G.M. Clarke, et al., "Comparative Gastrointestinal Transit of Pellet Systems of Varying Density" international Journal of Pharmaceutics vol. 114, Jan. 1995, pp. 1-11.

Garcia-Borreguero, et al., "Circadian Variation in Neuroendocrine Response to L-dopa in Patients with Restless Legs Syndrome", Sleep, vol. 27, No. 4, 2004, pp. 669-673.

Groning, et al., "Estimation of the gastric residence time of magnetic dosage forms using the Heidelberg capsule", Pharmazie, 51, 1996, pp. 328-331.

Gros, et al., "Obstructive Sleep Apnea in Parkinson's Disease Patients: Effect of Sinemet CR Taken at Bedtime", Sleep and Breathing vol. 20, (2016), Copyright 2015, 8 Pages.

Guan, et al., "A Novel Gastric-Resident Osmotic Pump Tablet: In Vitro and in Vivo Evaluation" International Journal of Pharmaceutics vol. 383, Jan. 2010, pp. 30-36.

Gupta, et al., "Preparation and characterization of superporous hydrogels as gastroretentive drug delivery system for rosiglitazone maleate", DARU vol. 18, No. 3 2010, pp. 200-210.

Gupta, et al., "Preparation and Characterization of Superporous Hydrogels as pHSensitive Drug Delivery System for Pantoprazole Sodium"; Current Drug Delivery, Oct. 2009; 6, pp. 505-510.

Hauser, et al., "Orally Inhaled Levodopa (CVT-301) for Early Morning OFF Periods in Parkinson's Disease", Parkinsonism and Related Disorders Jul. 2016, pp. 175-180.

Hsuan-Ming Yao, et al., "Clinical Pharmacokinetics of IPX066: Evaluation of Dose Proportionality and Effect of Food in Healthy Volunteers", Clinical Neuropharmacology, vol. 39, No. 1, Jan.-Feb. 2016, pp. 10-17.

Inbrija FDA Approved Labelling Dec. 21, 2018, 17 pages.

Kaplan, et al., "A Double-Blind, Placebo-Controlled Study of the Treatment of Periodic Limb Movements in Sleep Using Carbidopa/ Levodopa and Propoxyphene", Sleep 16(8), 1993, pp. 717-723.

Kuoppamaki, et al., "Comparison of Pharmacokinetic Profile of Levodopa Throughout the Day Between Levodopa / Carbiodopa / Entacapone and Levodopa / Carbidopa When Administered Four or Five Times Daily", European Journal of Clinical Pharmacology, Springer Verlag, 2009, 65(5), pp. 443-455.

Kuoppamaki, et al., "Night-Time Bioavailablity of Levodopa/ Carbidopa/Entacapone is Higher Compared to Controlled-Release Levodopa/Carbiodopa" International Journal of Clinical Pharmacology and Therapeutics, vol. 48 No. 11, 2010, pp. 756-760.

Leeman, et al., Parkinson's Disease in the Elderly: Response to and Optimal Spacing of Night Time Dosing with Levodopa, Br. J. clin. Pharmac. (1987) 24, pp. 637-643.

Mandal, et al., "Gastro-retentive drug delivery systems and their in vivo success: A recent update", Aian Journal of Pharmaceutical Sciences 11 (2016); pp. 575-584.

Menza, et al., "Sleep Disturbances in Parkinson's Disease", Mov Disord 25(Suppl 1), 2020, pp. S117-S122.

Montplaisir, et al., "Restless Legs Syndrome and Periodic Movements in Sleep: Physiopathology and Treatment with L-Dopa", Clinical Neuropharmacology, Oct. 1986, pp. 456-463.

Nyholm, et al., "Circadian Rhythmicity in Levodopa Pharmacokinetics in Patients with Parkinson Disease", Clinical Neuropharmacology & vol. 33, No. 4, Jul.-Aug. 2010, pp. 181-185.

Pal, et al., "A Review of Normal Sleep and Its Disturbances in Parkinson's Disease", Parkinsonism and Related Disorders 5, 1999, pp. 1-17.

Patel, el al., "Profile of Inhaled Levodopa and its Potential in the Treatment of Parkinson's Disease: Evidence to Date", Neuropsychiatric Disease and Treatment 14, 2018, pp. 2955-2964.

Poceta, et al., "Circadian Rhythm of CSF Monoamines and Hypocretin-1 in Restless Legs Syndrome and Parkinson's Disease", Sleep Medicine 10 (2009), pp. 129-133.

Puligheddu, et al., "Time Structure of Leg Movement Activity During Sleep in Untreated Parkinson Disease and Effects of Dopaminergic Treatment", Sleep Medicine 15 (2014), pp. 816-824.

Ritsuko Ito, et al., "Magnetic Granules: a Novel System for Specific Drug Delivery to Esophageal Mucosa in Oral Administration", international Journal of Pharmaceutics, vol. 61, Jun. 1990, pp. 109-117.

Smith, "An Overview of Sleep and Circadian Dysfunction in Parkinson's Disease", J Sleep Res. 2018 27 e 12673, 22 pages.

Sringean, et al., "How Well Do Parkinson's Disease Patients Turn in Bed? Quantitative Analysis of Nocturnal Hypokinesia Using Multisite Wearable Inertial Sensors", Parkinsonism and Related Disorders 23, 2016, pp. 10-16.

Stocchi, et al., "Efficacy of ND0612 for Nocturnal Problems and Early Morning OFF", Movement Disorders, vol. 33, Supp. Supplement, Abstract No. 231, Oct. 2018, 2 pages.

Stocchi, et al., "The Relevance of Dopaminergic Level in Nocturnal Disability in Parkinson's Disease: Implications of Continuous Dopaminergic Stimulation at Night to Treat the Symptoms", J Neural Transm (2014) 121 (Suppl 1): pp. S79-S83.

* cited by examiner

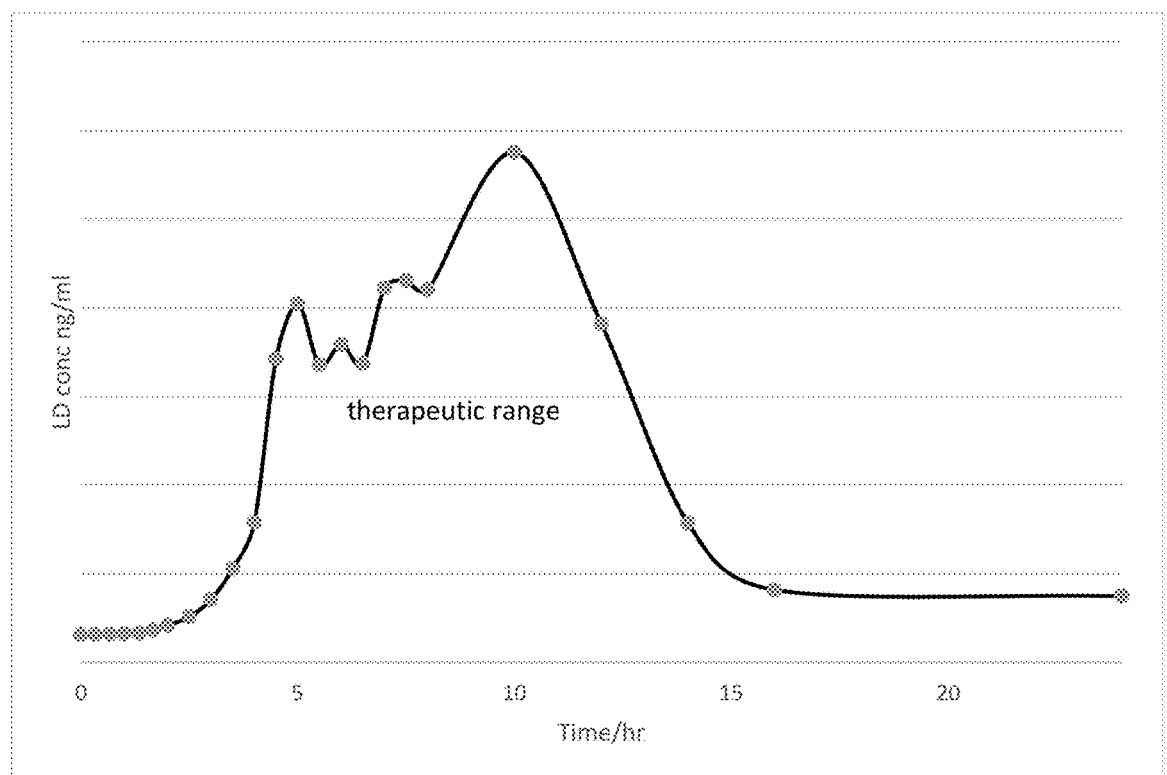

GASTRORETENTIVE TREATMENT OF NOCTURNAL SYMPTOMS AND MORNING AKINESIA IN SUBJECTS WITH PARKINSON'S DISEASE

CROSS REFERENCE TO RELATED APPLICATIONS

This application claims the benefits of U.S. Provisional Application No. 62/847,542, filed May 14, 2019, and U.S. Provisional Application No. 62/858,018, filed Jun. 6, 2019, the entireties of which are incorporated by reference herein.

TECHNICAL FIELD

The present disclosure pertains to compositions and methods for treating symptoms of Parkinson's disease.

BACKGROUND

Parkinson's disease (PD) is a common progressive neurodegenerative disorder of the Central Nervous System (CNS) that mainly affects a sufferer's motor function. Symptoms develop slowly over time and increase in severity as the disease becomes more advanced. In early stage PD, patients typically present with tremors and other motor symptoms. Changes in posture and facial expressions are also seen. As the disease progresses, the symptoms become progressively worse and patients suffer from rigidity, walking problems, loss of balance, a general slowing of movements and episodes of akinesia. Eventually the disease advances to debilitating levels where the patient might no longer be able to stand or walk. PD can also affect non-motor functions and is associated with dementia, sensory problems, autonomic dysfunction, and sleep and emotional problems.

The motor symptoms of PD are understood to be due to the death of striatal cells in the midbrain's substantia nigra. Damage to these cells results in a reduction in the availability of centrally active dopamine. The medical treatment of PD attempts to address this pathology and is typically divided into three groups:
1. Dopamine replacement therapy by systemic administration of its biological precursor, levodopa. Levodopa is usually administered in combination with DOPA decarboxylases and/or COMT inhibitors which assist in increasing the central bioavailability of levodopa.
2. Dopamine agonist therapy to mimic central dopamine activities.
3. MAO-B inhibitors to increase the central synaptic availability of dopamine.

As levodopa is actively absorbed in the small intestine by the large neutral amino acid transporter and once absorbed has a half-life of only 1.5 hours, currently approved levodopa monotherapy and combination oral dosage forms only provide therapeutic levels of the drug for a few hours per administration. A technical challenge therefore exists in providing a consistent delivery of levodopa to the small intestine and many approaches at gastric retention of the drug have been suggested.

It has been shown that the administration of levodopa after meals can delay the drug's release from the stomach and subsequent absorption. Reports have indicated that the delay in the identification of circulating plasma levodopa levels after meals is from 29 to 60 minutes for immediate release tablets (Baruzzi 1987) and from 30 to 75 minutes for controlled release tablets (Contin 1998) after administration.

Many patients treated with levodopa suffer from profound diurnal fluctuations in their psychomotor state where the relatively sudden drop in circulating plasma levels of levodopa at the end of a dose results in rest tremor, bradykinesia, and rigidity, a state commonly referred to as "off". The patient can also suffer from non-motor symptoms, such as fluctuations in cognition, attention, anxiety, depression, apathy, sweating, lightheadedness, abdominal pain, bloating, urinary urgency, visual disturbances, pain, dysesthesia, akathisia, and restless legs syndrome. Early morning akinesia, which may include bradykinesia, describes the morning slowness or immobility experienced prior to the first medication dose of the day that is experienced by many patients, especially those with more advanced disease. Chronic administration of levodopa can also induce dyskinesia in PD patients. Such levodopa induced dyskinesia (LID) is associated with neurodegeneration in cortical and subcortical areas, including the prefrontal cortex, primary motor cortex, striatum, subthalamic nucleus, and cerebellum.

Sleep disturbances are important non-motor manifestations in patients with (PD) at different stages of the course of the disease. Numerous forms of alterations of physiologic sleep patterns have been reported, ranging from increased daytime sleepiness after introduction of a dopamine agonist to the therapeutic regimen to specific sleep-related diagnoses (e.g., insomnia, vivid dreams, restless legs syndrome (RLS), rapid eye movement sleep behavior disorder (RBD), periodic limb movements (PLM), circadian rhythm disruption and excessive daytime sleepiness (EDS) or sleep-related breathing disorders (e.g., obstructive sleep apnea). The origin of these sleep disorders is multifactorial including degeneration of the brain areas that modulate sleep, the symptoms of the disease, and the effect of medications. These disturbances can primarily affect the patient's quality of life and may worsen the symptoms of PD. Other nocturnal non-motor manifestations of PD include cognitive dysfunction, hallucinosis, sensory and autonomic dysfunctions including orthostatic hypotension, urogenital dysfunction and constipation. These symptoms are prevalent in most PD patients e.g., between 60-80% of PD patients suffer from nocturnal urogenital dysfunction.

Studies have also shown that slow homeostatic adjustment of intrinsic excitability during sleep is very important for network stabilization. Spike-timing-dependent plasticity, such as long term potentiation, has a crucial role in network stability. Slow-wave activity (SWA) is considered to be the basis for overnight synaptic homeostatic processes, and is associated during non-rapid eye movement (NREM) sleep with fine adjustment of cortical excitability and plasticity. Impaired synaptic homeostasis during sleep has been found to be correlated with dyskinesia in both animal models of PD and clinical studies. In addition, it has been found that both early stage and advanced PD patients manifested clear-cut physiological decreases in SWA between early and late sleep whereas no such differential was found in LID sufferers suggesting that suggest that cortical SWA changes may be associated with the development of LID (Gelati 2018).

Dopamine levels in the cerebrospinal fluid have been shown to rise overnight to a maximum level at 6 am in normal subjects. In contrast, in PD patients, levels peak at 10 am and drop steadily over the following 24 hours, with the lowest levels and the greatest differential from normal subjects, occurring between the hours of 2 am and 6 am (Poceta 2009). Studies on the circadian rhythm of melatonin release have demonstrated that levodopa treated PD patients demonstrated an almost 2 hour earlier nocturnal melatonin peak, occurring around midnight, in comparison to either treatment naïve PD patients or normal subjects where the peak occurs around 2 am (Fertl 1993). Studies of 24-hour clock-gene expression in PD patients have shown a higher expression at 4 am when compared to normal subjects (Breen 2014).

Overnight treatment with levodopa, transdermal or long-acting dopamine agonists, or bilateral subthalamus stimulation, to improve sleep continuity and other nocturnal motor and non-motor manifestations of PD have been investigated. Studies of PD patients who were administered evening immediate release levodopa products have been shown to be somewhat effective in reducing nocturnal PD symptomologies in the earlier parts of the night, whereas those who were also administered a controlled release levodopa product demonstrated effectivity even into the later parts of the night (Collado-Seidel 1999, Gros 2015). Studies of 24-hour intestinal levodopa administration have suggested improvement in nocturnal akinesia (Ricciardi 2016), sleep quality (Nyholm 2005, WO2007/138086) and reductions in the time spent with dyskinesia (Cruse 2018). WO2012/059815 suggests the use of a specific formulation of levodopa administered at or before bedtime which to provide effective levodopa blood plasma levels throughout the night and an improvement in sleep quality over the night following administration. WO2002/000213 proposes the use of a specific formulation of levodopa administered in the evening, which would delay release of levodopa until the early morning hours before the patient awakens so that the patient would awaken when the therapeutic effect of the dose is near its maximum.

In contrast, high evening doses of dopaminomimetic medication cause sleep-onset insomnia and parasomnias and typically this problem is managed by either taking the drugs earlier in the evening or reducing the bedtime dose (Pal 1999). It has also been shown that higher amounts of dopaminergic medications, including levodopa monotherapy, taken by PD patients within 4 hours of bedtime negatively impacted sleep quality (Chahine 2013) and that no effect in the later parts of the night was shown for improvements in the time spent awake for controlled release levodopa products administered to PD patients prior to sleep (Wailke 2011). Furthermore, concerns have been raised about levodopa's potentially alerting effect and whether this might impair a PD patient's ability to enter into sleep (sleep initiation).

The pharmacokinetic profile of orally administered levodopa might be different between night-time and waking hours dosing. In a study of 8 PD patients taking immediate release levodopa combination products, it was found that the time to maximum peak was delayed and the maximum concentrations of levodopa were lower for the night-time dose, although the overall plasma exposure remained the same for both (Nyholm 2010). It was speculated that this effect might be the result of the subject's supine position when sleeping which has been noted to delay stomach opening, from increased levels of neutral amino acids in the evening and even from the circadian rhythmicity in gastrointestinal blood flow and enzymatic activity.

However, the fine balance between prevention of nocturnal PD symptomologies, treatment of morning akinesia, and avoiding overdosing and concomitant fluctuations in psychomotor state has made the ideal levodopa dosing strategy difficult to predict. Certain patients may benefit from additional dosing in order to address nocturnal symptoms, morning akinesia, or both, while others would not respond or may be thrown into symptomatic imbalance from such regimens.

Accordingly, there exists an outstanding need for treatments using levodopa that can be used without compromising the patient's regular daily dosing and yet assist in the treatment of their night-time symptomology and early morning akinesia/bradykinesia.

BRIEF SUMMARY

Provided herein are methods of treating nocturnal symptoms of Parkinson's disease, morning akinesia, or associated symptoms thereof, comprising administering to a human subject having Parkinson's disease a pharmaceutical composition comprising levodopa, wherein, following the administration, the composition does not provide identifiable circulating plasma levels of levodopa until at least two hours following administration, and said composition provides therapeutically effective circulating plasma levels of levodopa for at least five hours.

Also provided are pharmaceutical compositions for treating nocturnal symptoms of Parkinson's disease, morning akinesia, or associated symptoms thereof in a human subject having Parkinson's disease, wherein the composition comprises levodopa, and, wherein, following oral administration to the subject, said composition does not provide identifiable circulating plasma levels of levodopa until at least two hours following administration, and said composition provides therapeutically effective circulating plasma levels of levodopa for at least five hours.

BRIEF DESCRIPTION OF THE FIGURES

FIG. 1 illustrates the pharmacokinetic release profile of the GRDF of Example 1 after administration to healthy subjects.

DETAILED DESCRIPTION

The present inventions may be understood more readily by reference to the following detailed description taken in connection with the accompanying FIGURES and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a particle" is a reference to one or more of such particles and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to a value of 7.2% to 8.8%, inclusive. Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included." The phrase "at least about x" is intended to embrace both "about x" and "at least x". It is also understood that where a parameter range is provided, all integers within that range, and tenths thereof, are also provided by the invention. For example, "2-5 hours" includes 2 hours, 2.1 hours, 2.2 hours, 2.3 hours etc. . . . up to 5 hours.

The present disclosure provides, inter alia, methods of treating nocturnal symptoms of Parkinson's disease, morning akinesia, or associated symptoms thereof, comprising administering to a human subject having Parkinson's disease a pharmaceutical composition comprising levodopa, wherein following the administration, the composition does not provide identifiable circulating plasma levels of levodopa until at least two hours following administration, and said composition provides therapeutically effective circulating plasma levels of levodopa for at least five hours.

Also provided are pharmaceutical compositions for treating nocturnal symptoms of Parkinson's disease, morning akinesia, or associated symptoms thereof in a human subject having Parkinson's disease, wherein the composition comprising levodopa, wherein, following oral administration to the subject, said composition does not provide identifiable circulating plasma levels of levodopa until at least two hours following administration, and said composition provides therapeutically effective circulating plasma levels of levodopa for at least five hours.

As used herein, the term "levodopa" refers to the compound 3-hydroxy-L-Tyrosine, pharmaceutically acceptable salts, esters and isotopically enriched analogs or mixtures thereof. In a preferred embodiment, the term "levodopa" refers to the compound 3-hydroxy-L-Tyrosine.

As used herein, the term "identifiable circulating plasma levels of levodopa" refers to levels of levodopa, as measured by accepted analytical methods, of 10.5 ng/ml or higher.

In some embodiments, said compositions do not provide identifiable circulating plasma levels of levodopa for at least 2 hours after administration. In other embodiments, said compositions do not provide identifiable circulating plasma levels of levodopa for at least 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75 or 10 hours after administration.

As used herein, the term "provide therapeutically effective circulating plasma levels of levodopa" refers to levels of levodopa, as measured by accepted analytical methods, of at least 400 ng/ml.

In certain embodiments, the human subject having Parkinson's disease has early Parkinson's disease. In other embodiments, the human subject has moderate Parkinson's disease. In other embodiments, the human subject has advanced Parkinson's disease. The diagnosis of the extent of a human subject's Parkinson's disease is well known to those of skill in the art and can be established, for example, by reference to the Hoehn and Yahr scale, where, typically, scores of 1 and 2 represent early, 2 and 3 moderate, and 4 and 5 advanced Parkinson's disease.

In certain embodiments, compositions provide therapeutically effective circulating plasma levels of at least 400 ng/ml of levodopa. In another embodiment, said compositions provide therapeutically effective circulating plasma levels of at least 450, at least 500, at least 550, at least 600, at least 650, at least 700, at least 750, at least 800, at least 850, at least 900, at least 950, at least 1000, at least 1050, at least 1100 or of at least 1150 ng/ml of levodopa. In preferred embodiments, said compositions provide therapeutically effective circulating plasma levels of levodopa of at least 500 ng/ml. In other preferred embodiments, said compositions provide therapeutically effective circulating plasma levels of levodopa of at least 600 ng/ml. In other preferred embodiments, the compositions provide therapeutically effective circulating plasma levels of levodopa of at least 800 ng/ml.

In certain embodiments, said compositions provide therapeutically effective circulating plasma levels of levodopa of between at least 400 ng/ml and 1200 ng/ml. In other embodiments, said compositions provide therapeutically effective circulating plasma levels of between at least 450, at least 500, at least 550, at least 600, at least 650, at least 700, at least 750, at least 800, at least 850, at least 900, at least 950, at least 1000, at least 1050, at least 1100 or of between at least 1150 ng/ml and 1200 ng/ml of levodopa. In preferred embodiments, said compositions provide therapeutically effective circulating plasma levels of levodopa of between at least 600 ng/ml and 1200 ng/ml. In other preferred embodiments, said compositions provide therapeutically effective circulating plasma levels of levodopa of between at least 800 ng/ml and 1200 ng/ml.

In other preferred embodiments, said compositions provide therapeutically effective circulating plasma levels of levodopa of between at least 500 ng/ml and 800 ng/ml. In other preferred embodiments, said compositions provide therapeutically effective circulating plasma levels of levodopa of between at least 500 ng/ml and 1200 ng/ml.

In some embodiments, said compositions begin providing therapeutically effective circulating plasma levels of levodopa about 3 hours after administration. In other embodiments, said compositions begin providing therapeutically effective circulating plasma levels of levodopa about 3.25, about 3.5, about 3.75, about 4, about 4.25, about 4.5, about 4.75, about 5, about 5.25, about 5.5, about 5.75, about 6, about 6.25, about 6.5, about 6.75, about 7, about 7.25, about 7.5, about 7.75 or about 8 hours after administration.

In some embodiments, said compositions do not provide therapeutically effective circulating plasma levels of levodopa until at least 3 hours after administration. In other embodiments, said compositions do not provide therapeutically effective circulating plasma levels of levodopa until at least 3.25, at least 3.5, at least 3.75, at least 4, at least 4.25, at least 4.5, at least 4.75, at least 5, at least 5.25, at least 5.5, at least 5.75, at least 6, at least 6.25, at least 6.5, at least 6.75, at least 7, at least 7.25, at least 7.5, at least 7.75 or at least 8 hours after administration.

In some embodiments, said compositions do not provide identifiable circulating plasma levels of levodopa for at least 2 hours after administration and do not provide therapeutically effective circulating plasma levels of levodopa for at least 3 hours after administration. In other embodiments, said compositions do not provide identifiable circulating plasma levels of levodopa for at least 2 hours after administration and do not provide therapeutically effective circulating plasma levels of levodopa for at least 4 hours after administration. In other embodiments, said compositions do not provide identifiable circulating plasma levels of levodopa for at least 2 hours after administration and do not provide therapeutically effective circulating plasma levels of levodopa for at least 5 hours after administration. In other embodiments, said compositions do not provide identifiable circulating plasma levels of levodopa for at least 2 hours after administration and do not provide therapeutically effective circulating plasma levels of levodopa for at least 6 hours after administration. In other embodiments, said compositions do not provide identifiable circulating plasma levels of levodopa for at least 2 hours after administration and do not provide therapeutically effective circulating plasma levels of levodopa for at least 7 hours after administration. In other embodiments, said compositions do not provide identifiable circulating plasma levels of levodopa for at least 2 hours after administration and do not provide therapeutically effective circulating plasma levels of levodopa for at least 8 hours after administration.

In certain embodiments, said compositions provide therapeutically effective circulating plasma levels of levodopa for at least 5 hours. In other embodiments, said compositions provide therapeutically effective circulating plasma levels of levodopa for at least 5.25, at least 5.5, or at least 5.75, at least 6, at least 6.25, at least 6.5, at least 6.75, at least 7, at least 7.25, at least 7.5, at least 7.75, at least 8, at least 8.25, at least 8.5, at least 8.75, at least 9, at least 9.25, at least 9.5, at least 9.75, at least 10, at least 10.25, at least 10.5, at least 10.75, at least 11, at least 11.25, at least 11.5, at least 11.75 or at least 12 hours.

In certain embodiments, said compositions do not provide identifiable circulating plasma levels of levodopa for at least 2 hours after administration and wherein said compositions provide therapeutically effective circulating plasma levels of levodopa for at least 5 hours. In other embodiments, said compositions do not provide identifiable circulating plasma levels of levodopa for at least 2.25 hours after administration and wherein said compositions provide therapeutically effective circulating plasma levels of levodopa for at least 5 hours. In yet other embodiments, said compositions do not provide identifiable circulating plasma levels of levodopa for at least 2.5 hours after administration and wherein said compositions provide therapeutically effective circulating plasma levels of levodopa for at least 5 hours. In yet other embodiments, said compositions do not provide identifiable circulating plasma levels of levodopa for at least 2.75 hours after administration and wherein said compositions provide therapeutically effective circulating plasma levels of levodopa for at least 5 hours. In yet other embodiments, said compositions do not provide identifiable circulating plasma levels of levodopa for at least 3 hours after administration and wherein said compositions provide therapeutically effective circulating plasma levels of levodopa for at least 5 hours. In yet other embodiments, said compositions do not provide identifiable circulating plasma levels of levodopa for at least 3.25 hours after administration and wherein said compositions provide therapeutically effective circulating plasma levels of levodopa for at least 5 hours. In yet other embodiments, said compositions do not provide identifiable circulating plasma levels of levodopa for at least 3.5 hours after administration and wherein said compositions provide therapeutically effective circulating plasma levels of levodopa for at least 5 hours. In yet other embodiments, said compositions do not provide identifiable circulating plasma levels of levodopa for at least 3.75 hours after administration and wherein said compositions provide therapeutically effective circulating plasma levels of levodopa for at least 5 hours. In yet other embodiments, said compositions do not provide identifiable circulating plasma levels of levodopa for at least 4 hours after administration and wherein said compositions provide therapeutically effective circulating plasma levels of levodopa for at least 5 hours. In yet other embodiments, said compositions do not provide identifiable circulating plasma levels of levodopa for at least 4.25 hours after administration and wherein said compositions provide therapeutically effective circulating plasma levels of levodopa for at least 5 hours. In yet other embodiments, said compositions do not provide identifiable circulating plasma levels of levodopa for at least 4.5 hours after administration and wherein said compositions provide therapeutically effective circulating plasma levels of levodopa for at least 5 hours. In yet other embodiments, said compositions do not provide identifiable circulating plasma levels of levodopa for at least 4.75 hours after administration and wherein said compositions provide therapeutically effective circulating plasma levels of levodopa for at least 5 hours. In yet other embodiments, said compositions do not provide identifiable circulating plasma levels of levodopa for at least 5 hours after administration and wherein said compositions provide therapeutically effective circulating plasma levels of levodopa for at least 5 hours. In yet other embodiments, said compositions do not provide identifiable circulating plasma levels of levodopa for at least 5.25 hours after administration and wherein said compositions provide therapeutically effective circulating plasma levels of levodopa for at least 5 hours. In yet other embodiments, said compositions do not provide identifiable circulating plasma levels of levodopa for at least 5.25 hours after administration and wherein said compositions provide therapeutically effective circulating plasma levels of levodopa for at least 5 hours. In yet other embodiments, said compositions do not provide identifiable circulating plasma levels of levodopa for at least 5.5 hours after administration and wherein said compositions provide therapeutically effective circulating plasma levels of levodopa for at least 5 hours. In yet other embodiments, said compositions do not provide identifiable circulating plasma levels of levodopa for at least 5.75 hours after administration and wherein said compositions provide therapeutically effective circulating plasma levels of levodopa for at least 5 hours. In yet other embodiments, said compositions do not provide identifiable circulating plasma levels of levodopa for at least 6 hours after administration and wherein said compositions provide therapeutically effective circulating plasma levels of levodopa for at least 5 hours. In yet other embodiments, said compositions do not provide identifiable circulating plasma levels of levodopa for at least 6.25 hours after administration and wherein said compositions provide therapeutically effective circulating plasma levels of levodopa for at least 5 hours. In yet other embodiments, said compositions do not provide identifiable circulating plasma levels of levodopa for at least 6.5 hours after administration and wherein said compositions provide therapeutically effective circulating plasma levels of levodopa for at least 5 hours. In yet other embodiments, said compositions do not provide identifiable circulating plasma levels of levodopa for at least 6.75 hours after administration and wherein said compositions provide therapeutically effective circulating plasma levels of levodopa for at least 5 hours. In yet other embodiments, said compositions do not provide identifiable circulating plasma levels of levodopa for at least 7 hours after administration and wherein said compositions provide therapeutically effective circulating plasma levels of levodopa for at least 5 hours. In yet other embodiments, said compositions do not provide identifiable circulating plasma levels of levodopa for at least 7.25 hours after administration and wherein said compositions provide therapeutically effective circulating plasma levels of levodopa for at least 5 hours. In yet other embodiments, said compositions do not provide identifiable circulating plasma levels of levodopa for at least 7.5 hours after administration and wherein said compositions provide therapeutically effective circulating plasma levels of levodopa for at least 5 hours. In yet other embodiments, said compositions do not provide identifiable circulating plasma levels of levodopa for at least 7.75 hours after administration and wherein said compositions provide therapeutically effective circulating plasma levels of levodopa for at least 5 hours. In yet other embodiments, said compositions do not provide identifiable circulating plasma levels of levodopa for at least 8 hours after administration and wherein said compositions provide therapeutically effective circulating plasma levels of levodopa for at least 5 hours. In yet other embodiments, said compositions do not provide identifiable circulating plasma levels of levodopa for at least 8.25 hours after administration and wherein said compositions provide therapeutically effective circulating plasma levels of levodopa for at least 5 hours. In yet other embodiments, said compositions do not provide identifiable circulating plasma levels of levodopa for at least 8.5 hours after administration and wherein said compositions provide therapeutically effective circulating plasma levels of levodopa for at least 5 hours. In yet other embodiments, said compositions do not provide identifiable circulating plasma levels of levodopa for at least 8.75 hours after administration and wherein said compositions provide therapeutically effective circulating plasma levels of levodopa for at least 5 hours. In yet other embodiments, said compositions do not provide identifiable circulating plasma levels of levodopa for at least 9 hours after administration and wherein said compositions provide therapeutically effective circulating plasma levels of levodopa for at least 5 hours. In yet other embodiments, said compositions do not provide identifiable circulating plasma levels of levodopa for at least 9.25 hours after administration and wherein said compositions provide therapeutically effective circulating plasma levels of levodopa for at least 5 hours. In yet other embodiments, said compositions do not provide identifiable circulating plasma levels of levodopa for at least 9.5 hours after administration and wherein said compositions provide therapeutically effective circulating plasma levels of levodopa for at least 5 hours. In yet other embodiments, said compositions do not provide identifiable circulating plasma levels of levodopa for at least 9.75 hours after administration and wherein said compositions provide therapeutically effective circulating plasma levels of levodopa for at least 5 hours. In yet other embodiments, said compositions do not provide identifiable circulating plasma levels of levodopa for at least 10 hours after administration and wherein said compositions provide therapeutically effective circulating plasma levels of levodopa for at least 5 hours.

In certain embodiments, said compositions do not provide identifiable circulating plasma levels of levodopa for at least 2 hours after administration and wherein said compositions provide therapeutically effective circulating plasma levels of levodopa for at least 5.25 hours. In other embodiments, said compositions do not provide identifiable circulating plasma levels of levodopa for at least 2 hours after administration and wherein said compositions provide therapeutically effective circulating plasma levels of levodopa for at least 5.5 hours. In yet other embodiments, said compositions do not provide identifiable circulating plasma levels of levodopa for at least 2 hours after administration and wherein said compositions provide therapeutically effective circulating plasma levels of levodopa for at least 5.75 hours. In yet other embodiments, said compositions do not provide identifiable circulating plasma levels of levodopa for at least 2 hours after administration and wherein said compositions provide therapeutically effective circulating plasma levels of levodopa for at least 6 hours. In yet other embodiments, said compositions do not provide identifiable circulating plasma levels of levodopa for at least 2 hours after administration and wherein said compositions provide therapeutically effective circulating plasma levels of levodopa for at least 6.25 hours. In yet other embodiments, said compositions do not provide identifiable circulating plasma levels of levodopa for at least 2 hours after administration and wherein said compositions provide therapeutically effective circulating plasma levels of levodopa for at least 6.5 hours. In yet other embodiments, said compositions do not provide identifiable circulating plasma levels of levodopa for at least 2 hours after administration and wherein said compositions provide therapeutically effective circulating plasma levels of levodopa for at least 6.75 hours. In yet other embodiments, said compositions do not provide identifiable circulating plasma levels of levodopa for at least 2 hours after administration and wherein said compositions provide therapeutically effective circulating plasma levels of levodopa for at least 7 hours. In yet other embodiments, said compositions do not provide identifiable circulating plasma levels of levodopa for at least 2 hours after administration and wherein said compositions provide therapeutically effective circulating plasma levels of levodopa for at least 7.25 hours. In yet other embodiments, said compositions do not provide identifiable circulating plasma levels of levodopa for at least 2 hours after administration and wherein said compositions provide therapeutically effective circulating plasma levels of levodopa for at least 7.5 hours. In yet other embodiments, said compositions do not provide identifiable circulating plasma levels of levodopa for at least 2 hours after administration and wherein said compositions provide therapeutically effective circulating plasma levels of levodopa for at least 7.75 hours. In yet other embodiments, said compositions do not provide identifiable circulating plasma levels of levodopa for at least 2 hours after administration and wherein said compositions provide therapeutically effective circulating plasma levels of levodopa for at least 8 hours. In yet other embodiments, said compositions do not provide identifiable circulating plasma levels of levodopa for at least 2 hours after administration and wherein said compositions provide therapeutically effective circulating plasma levels of levodopa for at least 8.25 hours. In yet other embodiments, said compositions do not provide identifiable circulating plasma levels of levodopa for at least 2 hours after administration and wherein said compositions provide therapeutically effective circulating plasma levels of levodopa for at least 8.5 hours. In yet other embodiments, said compositions do not provide identifiable circulating plasma levels of levodopa for at least 2 hours after administration and wherein said compositions provide therapeutically effective circulating plasma levels of levodopa for at least 8.75 hours. In yet other embodiments, said compositions do not provide identifiable circulating plasma levels of levodopa for at least 2 hours after administration and wherein said compositions provide therapeutically effective circulating plasma levels of levodopa for at least 9 hours. In yet other embodiments, said compositions do not provide identifiable circulating plasma levels of levodopa for at least 2 hours after administration and wherein said compositions provide therapeutically effective circulating plasma levels of levodopa for at least 9.25 hours. In yet other embodiments, said compositions do not provide identifiable circulating plasma levels of levodopa for at least 2 hours after administration and wherein said compositions provide therapeutically effective circulating plasma levels of levodopa for at least 9.5 hours. In yet other embodiments, said compositions do not provide identifiable circulating plasma levels of levodopa for at least 2 hours after administration and wherein said compositions provide therapeutically effective circulating plasma levels of levodopa for at least 9.75 hours. In yet other embodiments, said compositions do not provide identifiable circulating plasma levels of levodopa for at least 2 hours after administration and wherein said compositions provide therapeutically effective circulating plasma levels of levodopa for at least 10 hours. In yet other embodiments, said compositions do not provide identifiable circulating plasma levels of levodopa for at least 2 hours after administration and wherein said compositions provide therapeutically effective circulating plasma levels of levodopa for at least 10.25 hours. In yet other embodiments, said compositions do not provide identifiable circulating plasma levels of levodopa for at least 2 hours after administration and wherein said compositions provide therapeutically effective circulating plasma levels of levodopa for at least 10.5 hours. In yet other embodiments, said compositions do not provide identifiable circulating plasma levels of levodopa for at least 2 hours after administration and wherein said compositions provide therapeutically effective circulating plasma levels of levodopa for at least 10.75 hours. In yet other embodiments, said compositions do not provide identifiable circulating plasma levels of levodopa for at least 2 hours after administration and wherein said compositions provide therapeutically effective circulating plasma levels of levodopa for at least 11 hours. In yet other embodiments, said compositions do not provide identifiable circulating plasma levels of levodopa for at least 2 hours after administration and wherein said compositions provide therapeutically effective circulating plasma levels of levodopa for at least 11.25 hours. In yet other embodiments, said compositions do not provide identifiable circulating plasma levels of levodopa for at least 2 hours after administration and wherein said compositions provide therapeutically effective circulating plasma levels of levodopa for at least 11.5 hours. In yet other embodiments, said compositions do not provide identifiable circulating plasma levels of levodopa for at least 2 hours after administration and wherein said compositions provide therapeutically effective circulating plasma levels of levodopa for at least 11.75 hours. In yet other embodiments, said compositions do not provide identifiable circulating plasma levels of levodopa for at least 2 hours after administration and wherein said compositions provide therapeutically effective circulating plasma levels of levodopa for at least 12 hours.

In some embodiments, the pharmaceutical composition comprises at least 300 mg of levodopa. In other embodiments, the pharmaceutical composition comprises at least 325 mg of levodopa. In yet other embodiments, the pharmaceutical composition comprises at least 350 mg of levodopa. In yet other embodiments, the pharmaceutical composition comprises at least 375 mg of levodopa. In yet other embodiments, the pharmaceutical composition comprises at least 400 mg of levodopa. In yet other embodiments, the pharmaceutical composition comprises at least 425 mg of levodopa. In yet other embodiments, the pharmaceutical composition comprises at least 450 mg of levodopa. In yet other embodiments, the pharmaceutical composition comprises at least 450 mg of levodopa. In yet other embodiments, the pharmaceutical composition comprises at least 475 mg of levodopa. In yet other embodiments, the pharmaceutical composition comprises at least 500 mg of levodopa. In yet other embodiments, the pharmaceutical composition comprises at least 525 mg of levodopa. In yet other embodiments, the pharmaceutical composition comprises at least 550 mg of levodopa. In yet other embodiments, the pharmaceutical composition comprises at least 575 mg of levodopa. In yet other embodiments, the pharmaceutical composition comprises at least 600 mg of levodopa. In yet other embodiments, the pharmaceutical composition comprises at least 625 mg of levodopa. In yet other embodiments, the pharmaceutical composition comprises at least 650 mg of levodopa. In yet other embodiments, the pharmaceutical composition comprises at least 675 mg of levodopa. In yet other embodiments, the pharmaceutical composition comprises at least 700 mg of levodopa. In yet other embodiments, the pharmaceutical composition comprises at least 725 mg of levodopa. In yet other embodiments, the pharmaceutical composition comprises at least 750 mg of levodopa. In yet other embodiments, the pharmaceutical composition comprises at least 775 mg of levodopa. In yet other embodiments, the pharmaceutical composition comprises at least 800 mg of levodopa.

In one embodiment, the pharmaceutical composition further comprises a DOPA decarboxylase inhibitor. Examples of DOPA decarboxylase inhibitors include benserazide and carbidopa. In one embodiment, the pharmaceutical composition comprises levodopa and a decarboxylase inhibitor and the (w/w) ratio of levodopa to DOPA decarboxylase inhibitor is 1:4. In another embodiment, the pharmaceutical composition comprises levodopa and a decarboxylase inhibitor and the (w/w) ratio of levodopa to DOPA decarboxylase inhibitor is 1:5. In another embodiment, the pharmaceutical composition comprises levodopa and a decarboxylase inhibitor and the (w/w) ratio of levodopa to DOPA decarboxylase inhibitor is between 1:5 and 1:10. In yet another embodiment, the pharmaceutical composition comprises levodopa and a decarboxylase inhibitor and the (w/w) ratio of levodopa to DOPA decarboxylase inhibitor is 1:10.

In some embodiments, the pharmaceutical composition further comprises a COMT inhibitor. Examples of COMT inhibitors include entacapone, opicapone and tolcapone. In a preferred embodiment, the COMT inhibitor comprises 200 mg of entacapone. In another preferred embodiment, the COMT inhibitor comprises 50 mg of opicapone. In another preferred embodiment, the COMT inhibitor comprises 100 mg of tolcapone. In yet another preferred embodiment, the COMT inhibitor comprises 200 mg of tolcapone.

In some embodiments, the pharmaceutical composition further comprises a DOPA decarboxylase inhibitor and a COMT inhibitor. In a preferred embodiment, the pharmaceutical composition comprises carbidopa and entacapone. In another preferred embodiment, the pharmaceutical composition comprises benserazide and entacapone. In yet another preferred embodiment, the pharmaceutical composition comprises carbidopa and tolcapone. In yet another preferred embodiment, the pharmaceutical composition comprises benserazide and tolcapone.

In certain embodiments, the pharmaceutical compositions comprises 400 mg of levodopa and 100 mg of carbidopa. In another embodiment, the pharmaceutical composition comprises 500 mg of levodopa and 125 mg of carbidopa. In yet another embodiment, the pharmaceutical composition comprises 600 mg of levodopa and 150 mg of carbidopa. In yet another embodiment, the pharmaceutical composition comprises 700 mg of levodopa and 175 mg of carbidopa.

The present disclosure is also directed to treating nocturnal symptoms of Parkinson's disease, morning akinesia, or associated symptoms thereof, comprising administering to a human subject having Parkinson's disease a pharmaceutical composition comprising levodopa, wherein, following said administration, said composition does not provide identifiable circulating plasma levels of levodopa until at least two hours following administration, and said composition provides therapeutically effective circulating plasma levels of levodopa for at least five hours.

As used herein, the term "nocturnal symptoms of Parkinson's disease" refers to those symptoms of Parkinson's disease that are present at night, typically when the patient is sleeping, trying to sleep or has woken up from sleep. Examples of nocturnal symptoms of Parkinson's disease include sleep disturbances, nocturia, nocturnal hypokinesia or akinesia, dribbling of saliva, pain, depression, nighttime hallucinations and confusion.

Examples of sleep disturbances include insomnia, vivid dreams, decreases in sleep quality, akathisia, rapid eye movement sleep behavior disorder (RBD), sleep disordered breathing, periodic limb movements (PLM), circadian rhythm disruption and excessive daytime sleepiness (EDS).

Insomnia is understood to be a recurrent difficulty to fall asleep (sleep initiation), stay asleep (sleep maintenance) and/or awakening too early in the morning. While all three problems occur in patients with PD, sleep maintenance difficulties are the most common, affecting up to 74-88% of patients. PD patients generally report two to five awakenings during the night (twice as many as are experienced by controls) with the patient being awake for 30-40% of the night.

In some embodiments, treatment of the nocturnal symptoms of Parkinson's disease includes the treatment of insomnia and consists of an improvement in PD patient's sleep initiation, in their sleep maintenance and/or in their early morning awakening.

Sleep quality is assessed by both subjective and objective measurements. Examples of subjective measures of sleep quality are the Parkinson's disease sleep scale (PDSS), the Parkinson's disease sleep scale-2 (PDSS-2), the Pittsburgh Sleep Quality Index (PSQI), the Scales for Outcomes in PD-Sleep Scale (SCOPA-S) and the NIMHANS comprehensive sleep disorder questionnaire (NCSDQ). Objective measurements of sleep quality are typically measured using polysomnography.

In some embodiments, treatment of the nocturnal symptoms of Parkinson's disease consists of the treatment of decreases in sleep quality and consists of improvements in PD patient's PDSS, in their PDSS-2, in their PSQI, in their SCOPA-S and/or in their NCSDQ scores. In a more preferred embodiment, the treatment consists of an improvement in patients' PDSS 1 (overall quality of night's sleep), in their PDSS 2 (sleep onset), in their PDSS 3 (maintenance and insomnia), in their PDSS 4 (nocturnal restlessness of limbs), in their PDSS 5 (fidgeting), in their PDSS 6 (distressing dreams), in their PDSS 7 (hallucinations), in their PDSS 8 (nocturia), in their PDSS 9 (urinary incontinence secondary to akinesia), in their PDSS 10 (numbness or tingling of limbs), in their PDSS 11 (muscle cramps), in their PDSS 12 (morning waking with painful posture), in their PDSS 13 (tremor upon waking), in their PDSS 14 (sleep refreshment), in their PDSS 15 (daytime dozing), in their PDSS-2 1 (overall quality of past week's sleep), in their PDSS-2 2 (sleep onset), in their PDSS-2 3 (maintenance and insomnia), in their PDSS-2 4 (nocturnal restlessness of limbs), in their PDSS-2 5 (fidgeting), in their PDSS-2 6 (distressing dreams), in their PDSS-2 7 (hallucinations), in their PDSS-2 8 (nocturia), in their PDSS-2 9 (discomfort secondary to akinesia), in their PDSS-2 10 (waking secondary to pain in limbs), in their PDSS-2 11 (waking secondary to muscle cramps), in their PDSS-2 12 (morning waking with painful posturing), in their PDSS-2 13 (tremor upon waking), in their PDSS-2 14 (sleep refreshment), in their PDSS-2 15 (waking secondary to snoring or difficulty in breathing), in their PSQI subjective sleep quality, in their PSQI sleep latency, in their PSQI sleep duration, in their PSQI sleep efficiency, in their PSQI sleep disturbance, in their PSQI use of sleep medication, in their PSQI daytime dysfunction, in their SCOPA-S nighttime sleep, in their SCOPA-S daytime sleepiness and/or in their SCOPA-S quality of sleep scores.

In some embodiments, treatment of the nocturnal symptoms of Parkinson's disease includes the treatment of decreases in sleep quality and consists of improvements in PD patients' total sleep time (TST)—defined as the time during time in bed (TIB) spent asleep, in their sleep efficiency (SE)—defined as the ratio of time spent asleep to TIB, in their sleep onset latency (SOL)—defined as the time from lights out to the first epoch of the N2 sleep stage, in their REM latency—defined as the time from the first epoch of the N2 sleep stage to the first epoch of REM sleep, in their wake after sleep onset (WASO)—defined as the time spent awake after the first N2 epoch during TIB, in their REM %, NREM 1%, NREM 2%, NREM 3%—defined as the ratios of time spent in particular sleep stages to TST, in their awakenings—defined as the number of awakenings (transitions to wake which lasts one epoch or longer) per hour of TIB, in their arousal index—defined as the number of arousals per hour of TIB, in their periodic limb movements index (PLMS)—defined as the number of PLM per hour of TIB, in their snore arousals index and/or in their apnea hypopnea index (AHI).

An increase in dreaming is common in PD, with studies suggesting that about 30% of patients develop vivid dreams on dopaminergic therapies. Examples of measurements of dreams include the Typical Dreams Questionnaire (TDQ), the Hall/Van de Castle system of quantitative dream content analysis, the Mannheim Dream questionnaire (MADRE), dream journals and PDSS and PDSS-2 6 scores.

In some embodiments, treatment of the nocturnal symptoms of Parkinson's disease includes the treatment of vivid dreams and consists of an improvement in PD patients' dream frequency, in their length, in their TDQ scores and/or in their MARDE scores.

Rapid eye movement sleep behavior disorder (RBD) is a syndrome of abnormal behavior during rapid eye movement (REM) sleep. Under normal circumstances, voluntary muscles are atonic when one enters REM sleep. However, the absence of this normal atonia in patients with RBD leads to the acting out of dreams. Thus, patients experience being chased in a dream and may flee the bed or attempt to punch their pursuer. The responses may range from relatively mild restlessness to more severe wild punching and thrashing in which patients may leap out of bed or strike their bed partner. RBD, of varying degrees of severity, occurs in 15-50% of patients with PD. One third of patients with PD have at least one episode of RBD per week. Assessment of RBD in PD patients is by clinical diagnosis, based upon symptoms reported by patients during a clinical interview, by elevated electromyographic tone on submental or limb derivations and/or by vocalizations and/or limb movements emerging out of REM sleep, without associated epileptiform activity on the EEG derivations, upon polysomnography. The International Classification of Sleep Disorders defines RBD as the patient suffering from both a) limb or body movement is associated with dream mentation and b) at least one of the following: harmful or potentially harmful sleep behaviors, dreams appear to be "acted out" or sleep behaviors disrupt sleep continuity. The definition is extended so that patients might also suffer from a) complaints of violent or injurious behavior during sleep, b) polysomnographic monitoring demonstrating at least one of the following: electrophysiologic measures during rapid eye movement (REM) sleep: excessive augmentation of chin (EMG) tone, excessive chin or limb phasic EMG twitching, irrespective of chin EMG activity and one or more of the following clinical features during REM sleep: excessive limb or body jerking, complex, vigorous, or violent behaviors, absence of epileptic activity in association with the disorder, c) the symptoms not being associated with mental disorders but may be associated with neurologic disorders and d) other sleep disorders (eg, sleep terrors or sleepwalking) can be present but are not the cause of the behavior.

In some embodiments, treatment of the nocturnal symptoms of Parkinson's disease includes the treatment of RBD and consists of an improvement in severity and/or frequency of PD patients' RBD.

Sleep disordered breathing may occur from a deficit in breathing drive in the brain (central sleep apnea) or a problem with the passage of air through the breathing passages (obstructive sleep apnea (OSA)). As breathing becomes more difficult or ceases, a decrease in blood oxygen level results, which in turn results in sufficient awakening to restore breathing. As the patient remains in light sleep, they may be unaware of these awakenings which may occur hundreds of times a night. Consequently, the patient experiences little deep restorative sleep at night and extreme daytime sleepiness. Apnea has been found in as many as 50% of patients with PD.

In some embodiments, treatment of the nocturnal symptoms of Parkinson's disease includes the treatment of sleep disordered breathing and consists of an improvement in PD patients' apnea-hypopnea index (AHI), in their respiratory arousal index (RAI), in their periodic limb movement arousal index (PLMAI), in their total arousal index (TAI) and/or in their oxygen desaturation index (ODI). In a preferred embodiment, treatment consisted of an improvement in PD patients' OSA severity from severe (AHI≥30/h) to moderate (30/h>AHI≥15/h) or mild (15/h>AHI≥5/h) or from in their severity from moderate to mild.

Periodic limb movements (PLM) are repetitive, non-epileptiform, movements of the lower limbs that show marked, age-dependent prevalence and appear to be at least partially under dopaminergic control. PLM is typically measured by surface mentalis electromyography, usually bilaterally of the anterior tibialis muscle. The total numbers of PLMs can be adjusted for a rate per hour to yield a PLM sleep Index (PLMS) and a PLM with arousal or Wakefulness Index (PLMW). In 1993, using electromyography, the American Sleep Association defined PLM as repetitive muscle jerks lasting from 0.5 to 5 seconds, separated by an interval ranging from 5 to 90 seconds, with an amplitude of at least 25% of that of the bursts recorded during prerecording calibration, organized in series of 4 or more consecutive leg movements (LM), usually recorded by applying surface electrodes over each anterior tibialis muscle 2 cm apart. Left and right leg LM are typically scored separately, and classified as bilateral LM when their intermovement interval is shorter than 5 seconds, and as monolateral LM, when it is longer. A PLMS index of 5 or more is generally understood to be clinically significant.

In some embodiments, treatment of the nocturnal symptoms of Parkinson's disease includes the treatment of PLM in PD patients and consists of improvements in their PLMS and/or in their PLMW indices. In a preferred embodiment, treatment consists of a reduction in PD patients' PLMS index from severe (>50) to moderate (>25 and <50) or mild (5 to <25). In another preferred embodiment, treatment consists of a reduction in PD patients' PLMS index from moderate to mild.

Akathisia, usually presenting as restless legs syndrome (RLS), is a neurological sensorimotor disease often profoundly disturbing sleep and quality of life. Definitions of RLS differ between various groups, however, the core features of RLS diagnosis across the different classifications are: (1) an urge to move the legs, (2) appearance of symptoms at rest, (3) relief by movement, and (4) prominence in the evening. Diagnostic criteria also require the exclusion of RLS mimics. Diagnostic questionnaires and objective analyses, such as actigraphy and PLMS analysis have been proposed for diagnosing and assessing RLS. However, typically, RLS remains a clinical diagnosis, based upon symptoms reported by patients during a clinical interview.

In some embodiments, treatment of the nocturnal symptoms of Parkinson's disease includes the treatment of akathisia and consists of an improvement in PD patients' presentation of RLS.

Circadian rhythm disruption in PD patients affects their sleep, blood pressure, heart rate, and levels of dopamine, cortisol and melatonin hormones and takes these cycles out of their normal synchronicity. In addition, hormone levels in PD patients have a reduced amplitude when compared to normal subjects.

In some embodiments, treatment of the nocturnal symptoms of Parkinson's disease includes the treatment of circadian rhythm disruption and consists of a return in PD patients' synchronicity of sleep, blood pressure, heart rate, dopamine, cortisol and/or melatonin to normal levels. In another embodiment, treatment consists of an increase in their circadian amplitude of dopamine, cortisol and/or melatonin.

Excessive daytime sleepiness (EDS) is a disabling trend to doze or fall asleep in various circumstances (e.g. reading, as a passenger in a car, during a meeting) that interferes with family, professional and social life. Sleepiness is usually self-assessed using the Epworth sleepiness scale. The scale measures the general level of daytime sleepiness (the sum of 8 item scores, 0-3) with a total score ranging from 0 to 24. The higher the ESS score, the higher the person's average sleep propensity in daily life and a score greater than 10 indicates abnormal sleepiness.

In some embodiments, treatment of the nocturnal symptoms of Parkinson's disease includes the treatment of EDS and consists of an improvement in PD patients' EDS. In a more preferred embodiment, the improvement is in PD patients' Epworth sleepiness scale. In an even more preferred embodiment, the improvement results in PD patients' Epworth sleepiness scale score to drop below 10.

Nocturia has been defined by the International Continence Society (ICS) in 2002 as "the complaint that the individual has to wake at night one or more times to void". It is generally understood that there are several causes for nocturia with the commonest causes being reduced functional bladder capacity and nocturnal polyuria (NP). These, however, are not mutually exclusive and often occur concurrently in the same patient, where the condition is known as mixed nocturia. Functional bladder capacity is reduced if the bladder wall compliance is reduced, if the detrusor is involuntarily contracting and/or if the bladder has incompletely emptied following a void and present clinically as frequent small-volume voids and/or urinary urgency. Measurement of functional bladder capacity is usually performed by urodynamic studies. NP is said to occur when rate of urine production is excessive only at night whereas 24-hour urine output remains within normal limits. The ICS defines NP as whenever the proportion of 24-hour urine voided at night is more than 20% of the entire 24-hour urine produced in young patients and 33% in the elderly, where the 24-hour volume is within normal limits (approximately 40 mL/kg).

In some embodiments, treatment of the nocturnal symptoms of Parkinson's disease includes the treatment of nocturia and consists of an improvement in PD patients' functional bladder capacity and/or their nocturnal polyuria. In a preferred embodiment, treatment of nocturia results in less than 33% of PD patients' 24-hour urine volume being voided at night.

Nocturnal hypokinesia/akinesia is a condition where PD patients have difficulty in moving their body during sleep so that rolling over or turning in bed and getting out of bed are restricted and might result in pain and/or the patient waking from sleep. The consequences of these long periods of immobilization and difficulty changing position include the development of pressure ulcers, predisposition to aspiration pneumonia, and asphyxia, which is a potential cause of death in PD patients. Hypokinesia and akinesia can be assessed using the Parkinson's Disease Quality of Life Questionnaire, the Unified Parkinson's Disease Rating Scale (UPDRS) Part III (motor examination) and/or a nocturnal hypokinesia questionnaire, or using actigraphy and/or by inertia sensors.

In some embodiments, treatment of the nocturnal symptoms of Parkinson's disease includes the treatment of nocturnal hypokinesia and/or akinesia in PD patients and consists of an improvement in their hypokinesia, or akinesia, questionnaire scores and/or in their actigraphy and/or inertia sensor findings.

Dribbling, or drooling, of saliva is found in between 30 and 50% of Parkinson's patients with an increased prevalence as the disease progresses. Nocturnal dribbling has been reported in up to 60% of Parkinson's patients with about 20% complaining that it presents even in the absence of diurnal dribbling. Dribbling is assessed by using the Movement Disorder Society Unified Parkinson's Disease Rating Scale (MDS-UPDRS) 2.2 (saliva and drooling) and/or the Radboud Oral Motor inventory for Parkinson's disease, subdomain saliva (ROMP-saliva) drooling severity scales.

In some embodiments, treatment of the nocturnal symptoms of Parkinson's disease includes the treatment of dribbling, or drooling, of saliva in PD patients and consists of an improvement in their nocturnal MDS-USDRS 2.2 and/or ROMP-saliva scores.

The prevalence of depression has been shown to be closely correlated with sleep disorders in Parkinson's disease patients. Compared to patients without depressive symptoms and controls, patients with depressive symptoms had significantly impaired scores in almost all PDSS subscores except PSDD 2 (difficulty in initiating sleep) and PDSS 11 (painful muscle clamp). Early morning tremor and nocturnal dystonia are also closely associated with depressive symptoms and depressive symptoms are exacerbated during periods of time in which patients experiences nocturnal wearing off related motor symptoms. Depression is assessed using the Montgomery and Asberg Depression Rating Scale (MADRS).

In some embodiments, treatment of the nocturnal symptoms of Parkinson's disease includes the treatment of depression in PD patients and consists of an improvement in their MADRS scores.

Nighttime hallucinations and confusion (sometimes referred to as psychosis) in PD patients, may result from any combination of cognitive impairment, dopaminergic medications, age and PD-related vision changes and lack of sleep. Psychosis may first appear after infection, trauma, surgery or prolonged hospitalization. Symptoms may range from a sensation that someone or something is standing at the side of or behind the person, to very detailed and often frightening visions. Delusions (often paranoid in nature) may occur as well.

In some embodiments, treatment of the nocturnal symptoms of Parkinson's disease includes the treatment of nighttime hallucinations and confusion in PD patients and consists of an improvement in the frequency and/or severity of their hallucinations and/or confused state.

As used herein, the term "early morning akinesia/bradykinesia" refers to the slowness and/or immobility experienced by PD patients upon waking in the morning and prior to the first medication dose of the day. Early morning akinesia/bradykinesia can significantly affect PD patient's quality of life (QoL) and impair their daily activities, such as arising from bed, dressing, bathing, toileting, preparing breakfast, and getting on with the day's work. Early morning akinesia/bradykinesia occurs in almost 60% of PD patients on dopaminergic treatment across all disease stages. Early morning akinesia/bradykinesia can be assessed by the Parkinson's Disease Quality of Life Questionnaire, the Unified Parkinson's Disease Rating Scale (UPDRS) Part III (motor examination) and/or a Time-to-ON Questionnaire.

In some embodiments, treatment of the early morning akinesia/bradykinesia of Parkinson's disease includes the improvement in the frequency of episodes of early morning akinesia/bradykinesia in PD patients and/or in their akinesia/bradykinesia questionnaire or scale scores. In a preferred embodiment, the improvement is in the patients' UPDRS Part 111.1 (speech), the UPDRS Part 111.2 (facial expression), the UPDRS Part 111.3 (tremor at rest), the UPDRS Part 111.4 (action or postural tremor of hands), the UPDRS Part 111.5 (rigidity), the UPDRS Part 111.6 (finger taps), the UPDRS Part 111.7 (hand movements), the UPDRS Part 111.8 (rapid, alternating movements of hands), the UPDRS Part 111.9 (leg agility), the UPDRS Part III.10 (arising from chair), the UPDRS Part III.11 (posture), the UPDRS Part 111.12 (gait), the UPDRS Part 111.13 (postural stability) and/or the UPDRS Part 111.14 (body bradykinesia and hypokinesia) scores.

As used herein, the term "associated symptoms" of early morning akinesia/bradykinesia refers to those non-motor symptoms commonly associated with early morning akinesia/bradykinesia. Examples of associated symptoms of early morning akinesia/bradykinesia include urinary urgency, anxiety, dribbling of saliva, pain, low mood, limb paresthesia, and dizziness.

In some embodiments, treatment of the associated symptoms of early morning akinesia/bradykinesia of Parkinson's disease patients includes the improvement in their functional bladder capacity, in their anxiety, in their MDS-USDRS 2.2 and/or ROMP-saliva scores, in their pain, in their mood, in their limb paresthesia and/or in their suffering from dizziness.

The pharmaceutical compositions of the present invention, and their administration in providing methods of treatment, consist of compositions which do not provide identifiable circulating plasma levels of levodopa for at least 2 hours after administration and which do provide therapeutically effective circulating plasma levels of levodopa for at least 5 hours.

In some embodiments, the composition is administered together with, or immediately following, the PD patient's evening meal. In other embodiments, the composition is administered within the hour before the PD patient goes to sleep in the evening.

In some embodiments of the present disclosure, the composition is administered either together with, or immediately following, the PD patient's evening meal, or, alternatively, within the hour before the PD patient goes to sleep in the evening, and provides therapeutically effective circulating plasma levels of levodopa for at least 5 hours whilst not providing identifiable circulating plasma levels of levodopa for at least 2 hours after said administration.

As used herein, the term "administered together with, or immediately following the Parkinson's disease patient's evening meal" refers to administration of the composition together with, or within 60 minutes of the PD patient's evening meal. In the event that the PD patient's evening meal is held four or more hours before the patient goes to bed, the evening meal takes the form of a snack or light meal eaten, for example, within the hour before the PD patient goes to sleep in the evening. Therefore, in some embodiments, the "evening meal" constitutes a snack or light meal, by which is meant any food representing more than "light" caloric intake as defined by a meal of at least 400 calories with at least a 20% fat content, that the patient consumes within four hours of when the patient retires to bed for sleep in the evening.

In some embodiments of the present disclosure, the composition does not provide therapeutically effective circulating plasma levels of levodopa until after midnight. In a preferred embodiment, the composition does not provide therapeutically effective circulating plasma levels of levodopa until after 1 am. In a more preferred the composition does not provide therapeutically effective circulating plasma levels of levodopa until after 2 am.

In some embodiments of the present disclosure, the composition provides therapeutically effective circulating plasma levels of levodopa between the hours of 6-8 am. In another embodiment, the composition provides therapeutically effective circulating plasma levels of levodopa between the hours of 5-7 am, between the hours of 4-6 am, the hours of 4-7 am, the hours of 4-8 am, the hours of 4-9 am, the hours of 4-10 am, the hours of 3-6 am, the hours of 3-7 am, the hours of 3-8 am, the hours of 3-9 am, the hours of 3-10 am, the hours of 2-6 am, the hours of 2-7 am, the hours of 2-8 am, the hours of 2-9 am, the hours of 2-10 am, the hours of 1-6 am, the hours of 1-7 am, the hours of 1-8 am, the hours of 1-9 am, the hours of 1-10 am, the hours of midnight-6 am, the hours of midnight-7 am, the hours of midnight-8 am, the hours of midnight-9 am and/or the hours of midnight-10 am.

For the pharmaceutical compositions of the present invention to provide therapeutically effective circulating plasma levels of levodopa for at least 5 hours, whilst not providing identifiable circulating plasma levels of levodopa for at least 2 hours after administration, they typically utilize properties of both gastric-retention and delayed release technologies.

Gastroretentive technologies allow for orally administered pharmaceutical compositions to have an extended gastric residence time. This formulatory approach is designed to allow for extended absorption of drugs which are either absorbed, or pharmacologically active, in the stomach, or drugs, such as levodopa, which are absorbed, or pharmacologically active, in the proximal small intestine. In addition, gastroretentive formulations have been shown to improve pharmacokinetic profiles for products with short half-lives that have the tendency to be eliminated quickly from the systemic circulation.

Examples of gastroretentive technologies include a) high density formulations which are heavy and dense enough to withstand in vivo peristaltic movement yet remain intact in spite of the gastrointestinal disturbances b) formulations containing magnetic elements and the application of an external magnet positioned on the abdomen c) swelling and/or expandable compositions which are designed to increase in size to become bigger than the diameter of pyloric sphincter and remain logged there until they are biodegraded d) floating tablets and gels where the bulk density of the formulation attains less than the density of gastric fluid after a certain lag time e) mucoadhesive gels which attach inside the lumen of the stomach wall f) mechanically expanding devices which open once inside the stomach to become larger than the diameter of the pyloric sphincter.

Further examples of gastroretentive technologies include Guan (2009), Devereux (1990) Clarke (1995), Ito (1990), Fujimori (1991), Groning (1996), Gupta (2009), Gupta (2010), WO2015083171, US20120077878, WO2011090725, WO2010019915, WO2008030830, WO2007072495, WO2005101983, WO2005079752, WO2004032906, WO0110419, WO2003035029, WO0200213, WO2001097783, WO2000038655, WO2000038650, US20030049325, U.S. Pat. Nos. 4,126,672, 4,814,179, WO2018232413, WO2016066256, WO2014060952, WO2014014348, WO2013054285, US20130017264, WO2012159077, WO2012004231, WO2011004799, WO2009153632, WO2008087882, WO2007106960, WO2006063858, WO2003037299, WO2003011255, WO2001058424, WO1999007342, EP3398615, WO2016087952, WO2013090893, WO2012070028, WO2005056708, WO2005007074, US20050013863, WO2003089506, EP1238663, WO1998052547, WO2012059815, US20110066175, WO2010035273, WO2009144558, WO2008027945, WO2003105812, WO2017096054, WO2015187746, WO2018102799, U.S. Pat. Nos. 4,735,804, 5,002,772, EP1915990, each of which is incorporated, in their entirety, herein by reference.

In some embodiments of the present disclosure, the pharmaceutical composition for providing therapeutically effective circulating plasma levels of levodopa for at least 5 hours, whilst not providing identifiable circulating plasma levels of levodopa for at least 2 hours after administration consists of a gastroretentive formulation. In a preferred embodiment, the composition is a high-density gastroretentive formulation. In another preferred embodiment, the composition is a magnetic element containing a gastroretentive formulation which is used in combination with an externally applied magnet. In yet another preferred embodiment, the composition is a swellable gastroretentive formulation. In yet another preferred embodiment, the composition is a floating tablet and/or gel gastroretentive formulation. In yet another preferred embodiment, the composition is a mucoadhesive gastroretentive formulation. In yet another preferred embodiment, the composition is a mechanically expandable gastroretentive formulation.

Delayed release technologies allow for orally administered pharmaceutical compositions to delay the release of their API, typically so that the release is controlled to occur either after a predetermined time period later than that of a conventional immediate release product and/or at a specific location along the gastrointestinal tract. The delayed release technologies of the present invention are typically designed to delay release of the composition's levodopa whilst maintaining the ability to release the levodopa in PD patient's stomachs after said delay. This is in contrast to many, commonly found, delayed release technologies that are designed to release their API at specific locations along the gastrointestinal tract, most commonly along both the small and large intestines, or only at the large intestine.

Time controlled delayed release compositions are typically designed to erode either due to bulk or surface erosion of the composition.

In one embodiment, bulk erosion compositions are understood to refer to compositions wherein the entry of water into the composition is faster than the rate of its degradation. Degradation then takes place throughout the polymer sample and proceeds until a critical molecular weight is reached. At this point, degradation products become small enough to be solubilised and the structure starts to become significantly more porous and hydrated allowing for release of the composition's API.

In one embodiment, surface erosion compositions are understood to refer to compositions which are coated with a soluble or erodible layer, which dissolves after time and releases the levodopa after a specified lag period. When this system comes in contact with an aqueous medium, the coat emulsifies and only erodes after the lag-time. Such compositions can be independent of gastrointestinal motility, pH, enzyme and/or gastric residence and their lag time are typically controlled by the thickness and the viscosity grade of the polymer used.

Coatings for surface erosion compositions are well known in the art and typically comprise non pH dependent polymers such as cellulose esters, cellulose acetate, cellulose acetate butyrate, ethylcellulose, Eudragit® RS and Eudragit® RL poly (ethyl acrylate-co-methyl methacrylate-cotrimethylammonioethyl methacrylate chloride), Eudragit® NE30D, Eudragit® NE40D or Eudragit® NM30D poly(ethyl acrylate-co-methyl methacrylate), ethyl acrylate methyl methacrylate copolymer, polyvinyl acetate and combinations thereof.

Stimuli controlled delayed release compositions are typically designed to release levodopa in response to a stimuli that might be induced by the biological environment, such as changes in temperature and chemical stimuli such as pH, enzymes or other chemicals. Alternatively, stimuli controlled delayed release compositions consist of osmotic pump systems which are timed to release their composition's API after osmotic absorption of a predefined quantity of fluid.

In one embodiment, pH controlled delayed release compositions may be soluble or erodible in a fluid such as fasting gastric juices, acidic fluids, and/or polar liquids, and insoluble and/or unerodible in the fluid of gastric juices in the period immediately following a meal, intestinal juices, substantially pH neutral or basic fluids and/or apolar liquids. In addition to utilizing the differential solubility of levodopa at the pH of fasting and fed gastric juices, various techniques can be employed to provide for such a pH controlled delayed release composition, including coating the composition with a polymer, such as a Eudragit E® (dimethylaminoethyl methacrylate, butyl methacrylate, and methyl methacrylate copolymer) which dissolves at the pH of fasting gastric juices but remains as a coating when exposed to the fluid of gastric juices in the period immediately following a meal. Alternatively, the composition itself can contain significant quantities of basic materials, such as magnesium hydroxide, magnesium trisilicate, aluminum hydroxide, magnesium oxide, barium sulfate, sodium acetate, magnesium L-arginine or magnesium meglumine, whose solubility is higher at lower pHs. Alternatively, the composition can consist of a cationic hydrogel, which imparts high water solubility at acidic pH and low water solubility at higher or neutral pHs. Alternatively, the composition can be administered within a pH sensitive capsule, which limits the release of the drug at higher pHs. Alternatively, the composition can utilize properties of the gastroretentive technology itself to improve the delayed release profile. For example, the composition could utilize the swellable properties of a cationic hydrogel to provide for a pH sensitive gastroretentive delayed release composition, or it could utilize the restricted surface area of the exposed drug, or the drug's zero order release profile, as found within floating tablet and/or gel gastroretentive compositions and/or mechanically expandable gastroretentive compositions, to improve the delayed release profile.

The present disclosure will be better understood by reference to the Examples, which follow, but those skilled in the art will readily appreciate that the specific experiments detailed are only illustrative as described more fully in the claims which follow thereafter.

Example 1: Manufacture of Gastroretentive Delayed Release Composition

A gastroretentive system was manufactured according to the procedures described in WO2018102799, which is incorporated in its entirety, herein, by reference. The formulation of the erodible tablet inserted into the system is described in Table 1.

TABLE 1

| Component | % of total weight including capsule |
|---|---|
| Levodopa Ph. Eur | 4.83 |
| Carbidopa USP | 1.30 |
| Povidone USP (PVP K-90) ISP | 3.48 |
| Mannitol USP (PEARLITOL 200SD) | 8.54 |
| Barium Sulfate USP | 10.34 |
| Ethylcellulose NF (Ethocel Premium 7 CPS) | 5.94 |
| Magnesium Stearate NF/BP (LIGAMED MF-2-V) | 0.35 |

Example 2: Single Dose, Partly Randomized, Open Label, 2 Sequence, Crossover Pharmacokinetic Study Eighteen healthy adult male or non-childbearing potential female, ≥35 and ≤70 years of age, BMI>20 and <30 kg/m$^2$, non-smokers, received 1× Sinemet® 100/25 mg levodopa/carbidopa tablet administered under fasting conditions of at least 10 hours Blood samples were collected at 24 different time points between pre-dose and 24 hours post administration and assayed for plasma levodopa concentration. After a washout period of at least 48 hours, the subjects were administered the composition of Example 1 30 minutes after a high-fat, high calorie, meal. Blood samples were collected at 24 different time points between pre-dose and 24 hours post administration and assayed for plasma levodopa concentration and subjects were also examined by fluoroscopy at 10 minutes, 4 and 8 hours post administration.

After administration of the composition of Example 1, no identifiable circulating plasma levels of levodopa were found for 2.3 hours. Therapeutically effective levels of levodopa were only found after 5.5 hours and remained at these levels for more than 8 hours. The graph of the pharmacokinetic release profile of the GRDF of Example 1 is shown in FIG. 1. Radiographic examination revealed that each GDRF was fully open and extended within the stomach within 10 minutes of administration and still present in the stomach at least 8 hours later.

Example 4: Clinical Study of Reduction in Morning Akinesia

The efficacy and safety of a delayed release gastroretentive formulation of 500 mg levodopa and 125 mg carbidopa is assessed in a 12 week placebo controlled, double blind study of 240 patients. At baseline, patients have at least 2 hours per day of OFF time and experience morning akinesia at least 15 days of every month. Patients are further randomized to receive their medication, either placebo (120 patients) or the delayed release gastroretentive formulation (120 patients), either within an hour of taking their evening meal or in the hour preceding their going to sleep. The primary endpoint is a change from placebo in the Unified Parkinson's Rating Scale (UPDRS) Part III motor score at 30 minutes after waking the following morning.

What is claimed:

1. A method of treating nocturnal symptoms of Parkinson's disease, morning akinesia, or associated symptoms of morning akinesia, in a human subject in need thereof, comprising
administering to the human subject a gastroretentive device comprising a pharmaceutical composition comprising levodopa, wherein, following said administration, said composition does not provide identifiable circulating plasma levels of levodopa until at least two hours following administration, and said composition provides therapeutically effective circulating plasma levels of levodopa for at least five hours.

2. The method according to claim 1, providing therapeutically effective circulating plasma levels of levodopa for about 6-10 hours.

3. The method according to claim 1, providing therapeutically effective circulating plasma levels of levodopa for about 7-9 hours.

4. The method according to claim 1, wherein therapeutically effective circulating plasma levels of levodopa are not identifiable for at least three hours following administration.

5. The method according to claim 1, wherein therapeutically effective circulating plasma levels of levodopa are identifiable about three hours following administration.

6. The method according to claim 1, wherein the gastroretentive device is administered together with, or immediately following, consumption of an evening meal by the subject.

7. The method according to claim 1, wherein the gastroretentive device is administered to the subject within one to four hours before the subject retires to bed for sleep.

8. The method according to claim 7, wherein the gastroretentive device is administered to the subject in the evening and therapeutically effective circulating plasma levels of levodopa are not identifiable until after midnight.

9. The method according to claim 8, wherein therapeutically effective circulating plasma levels of levodopa are identifiable between the hours of 6 am to 8 am.

10. The method according to claim 1, wherein therapeutically effective circulating plasma levels of levodopa are identifiable about 8-14 hours following the administration of the gastroretentive device.

* * * * *